United States Patent [19]
Mich

[11] 4,092,309
[45] May 30, 1978

[54] DERIVATIVES OF AMOXICILLIN
[75] Inventor: Thomas Frederick Mich, Ann Arbor, Mich.
[73] Assignee: Warner-Lambert Company, Morris Plains, N.J.
[21] Appl. No.: 791,270
[22] Filed: Apr. 27, 1977
[51] Int. Cl.² .......................................... C07D 499/68
[52] U.S. Cl. .................................. 260/239.1; 424/271
[58] Field of Search ...................................... 260/239.1
[56] References Cited
U.S. PATENT DOCUMENTS
3,873,523  3/1975  Doub et al. ...................... 260/239.1
3,954,734  5/1976  Doub et al. ....................... 260/239.1

Primary Examiner—Gerald A. Schwartz
Attorney, Agent, or Firm—Stephen Raines; David B. Ehrlinger; Frank S. Chow

[57] ABSTRACT

Derivatives of amoxicillin having broad spectrum antibacterial activity are disclosed. In addition, the following methods for preparing the compounds are provided (a) reacting the free amino acid amoxicillin or the acid salt or silylated derivative thereof with a reactive derivative of 6-(4-pyridyl)-1,2-dihydro-2-oxonicotinic acid and (b) reacting the free amino acid 6-aminopenicillanic acid or the acid salt or silylated derivative thereof with a reactive derivative of the corresponding D-(+)-N-(1,2-dihydro-2-oxonicotinyl)-2-(p-hydroyphenyl)glycine.

3 Claims, No Drawings

DERIVATIVES OF AMOXICILLIN

SUMMARY AND DETAILED DESCRIPTION

The present invention relates to novel chemical compounds that are useful as pharmacological agents and to methods for their production. More particularly, the invention relates to a novel organic amide having the formula

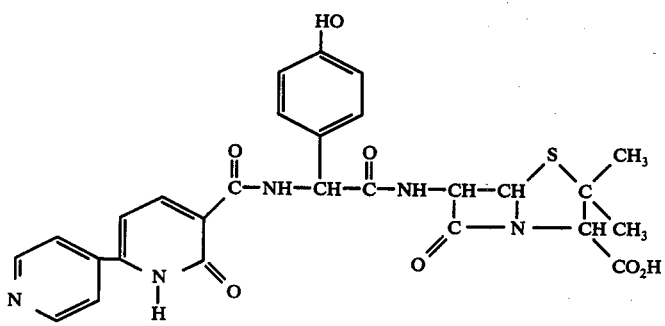

I and pharmaceutically-acceptable salts thereof.

In accordance with the invention, the foregoing amide having the formula I and pharmaceutically-acceptable salts thereof are produced by reacting the free amino acid amoxicillin or an acid salt, solvent complex or silylated derivative thereof with a reactive derivative of 6-(4-pyridyl)-1,2-dihydro-2-oxonicotinic acid. This is the preferred method.

For the reaction the 6-(4-pyridyl)-1,2-dihydro-2-oxonicotinic acid can be employed in activated form by using a carbodiimide, such as N,N'-dicyclohexylcarbodiimide. Some examples of other reactive derivatives of 6-(4-pyridyl)-1,2-dihydro-2-oxonicotinic acid suitable for the reaction are the acid halides, the imidazolide, mixed anhydrides (especially those formed from an alkyl chloroformate such as ethyl chloroformate and isobutyl chloroformate), and activated esters such as the pentachlorophenyl ester and the N-hydroxysuccinimide ester. The reactants are normally employed in approximate equimolar quantities, although an excess of either can be used if desired. The reaction can be carried out in any of a number of unreactive solvents which may include tertiary amides (such as N,N-dimethylacetamide, dimethylformamide, and N-methyl-2-pyrrolidinone), ethers (such as dioxane, tetrahydrofuran, and 1,2-dimethoxyethane), chlorinated hydrocarbons (such as chloroform and dichloromethane), dimethylsulfoxide and mixtures of these. When using the silylated derivative for the reaction the solvent must be anhydrous. In addition to any of these solvents, when using amoxicillin for the reaction in the free acid or salt form, aqueous solutions may be used for acylation with an acid halide or mixed anhydride under normal Schotten-Baumann conditions. The duration and temperature of the reaction are not critical. Temperatures in the range from −50° to 40° C. are commonly used for reaction times ranging from about one hour up to about 24 hours. The product may be isolated in any suitable way as the free acid or as a salt by appropriate adjustment of the pH.

The 6-(4-pyridyl)-1,2-dihydro-2-oxonicotinic acid and its reactive derivatives which are required as starting materials in the foregoing process can be prepared according to any of a variety of methods as illustrated in greater detail hereinafter. The silylated amoxicillin starting materials can be prepared by reacting the amoxicillin or a salt thereof preferably in anhydrous form with either one, two or three equivalents of a tri(lower alkyl) silyl chloride in the presence of triethylamine or with other recognized silylating agents. The preferred silylating agent is trimethylsilyl chloride or bis(trimethylsilylacetamide). When three equivalents of the silylating agent are used, the amino, the hydroxyl, and the carboxyl group become silylated. When two equivalents are used, the hydroxyl and the carboxyl groups are silylated. When one equivalent is used only the carboxyl group is silylated. The mono-, di-, and trisilylated products are fully reactive with the activated acids. The trisilylated product is preferred over the di- or monosilylated product as a starting material. After acylation the silyl groups are easily removed by treatment with water.

Also in accordance with the invention, the foregoing amide of the formula I and pharmaceutically-acceptable salts thereof are produced by reacting the free amino acid 6-aminopenicillanic acid or the corresponding acid salt, solvent complex or silylated derivative thereof with a reactive derivative of D-(+)-N-[6-(4-pyridyl)-1,2-dihydro-2-oxonicotinyl]-2-(p-hydroxyphenyl)glycine.

Some examples of reactive derivatives of the D-(+)-N-[6-(4-pyridyl)-1,2-dihydro-2-oxonicotinyl]-2-(p-hydroxyphenyl)-glycine compounds suitable for the reaction are the acid halides, the imidazolide, mixed anhydrides (especially those formed from an alkyl chloroformate such as ethyl chloroformate and isobutyl chloroformate), and activated esters such as the pentachlorophenyl ester and the N-hydroxysuccinimide ester. The reactants are normally employed in approximate equimolar quantities, although an excess of either can be used if desired. The reaction can be carried out in any of a number of unreactive solvents which may include tertiary amides (such as N,N-dimethylacetamide, dimethylformamide, and N-methyl-2-pyrrolidinone), ethers (such as dioxane, tetrahydrofuran, and 1,2-dimethoxyethane), chlorinated hydrocarbons (such as chloroform and dichloromethane), dimethylsulfoxide and mixtures of these. When using the silylated derivative for the reaction the solvent must be anhydrous. In addition to any of these solvents, when using 6-aminopenicillanic acid in the free acid or salt form, aqueous solutions may be used for acylation with an acid halide or mixed anhydride under normal Schotten-Baumann conditions. The duration and temperature of the reaction are not critical. Temperatures in the range from −50° to 40° C. are commonly used for reaction times ranging from about one hour up to about 24 hours. The product may be isolated in any suitable way as the free acid or as a salt by appropriate adjustment of the pH.

The D-(+)-N-[6-(4-pyridyl)-1,2-dihydro-2-oxonicotinyl]-2-(p-hydroxyphenyl)glycine and its reactive derivatives which are required as starting materials in the foregoing process can be prepared by methods illustrated in greater detail hereinafter. The silylated amino acid starting materials can be prepared by reacting the anhydrous 6-aminopenicillanic acid with a tri(lower alkyl)silyl chloride in the presence of triethylamine or with other recognized silylating agents, such as hexaalkyldisilazane. The preferred silylating agent is hexamethyldisilazane. Only the carboxyl group is silylated under the conditions used (e.g., 2-hour reflux in chloroform). After acylation, the silyl group is easily removed by treatment with water.

The free acids of the invention form carboxylate salts with any of a variety of inorganic and organic bases. Pharmaceutically-acceptable carboxylate salts are formed generally by reacting the free acids with such bases as sodium hydroxide, sodium carbonate, sodium bicarbonate, potassium hydroxide, potassium carbonate, calcium carbonate, ethylamine, 2-hydroxyethylamine, triethylamine and procaine. Preferred carboxylate salt forms are the alkali metal salts. The carboxylate salts are converted to the free acids by acidification. The free acids and their carboxylate salts usually differ somewhat in solubility properties but, in general, are otherwise equivalent for the purposes of the invention.

In addition, the compounds of this invention can exist in the form of acid-addition salt by using acids such as hydrochloric or sulfuric acid.

In addition, the compounds of this invention may exist in solvated, especially hydrated forms and these compounds are intended to be included within the compounds of the invention.

The compounds of the invention are new chemical compounds that are used as pharmacological agents and especially as broad spectrum antibacterial agents. They are active in vitro against strains of both gram-positive and gram-negative bacteria. Of special interest is the high degree of activity against *Pseudomonas aeruginosa*. More specifically, the protective dose for 50 percent of the mice against Pseudomonas aeruginosa by the subcutaneous route is 66 mg./kg. of body weight.

The invention is illustrated by the following examples.

EXAMPLE 1

A stirred solution of 13.9 g. of amoxicillin dimethylsulfoxide complex in 60 ml. of N,N-dimethylacetamide is cooled to 0–5° C. and 6.7 g. of 6-(4-pyridyl)-1,2-dihydro-2-oxonicotinylimidazolide is added, followed by 2.8 ml. of triethylamine. The mixture is stirred at room temperature for 1 hour 45 minutes, then poured into 300 ml. of chipped ice and water containing 20 ml. of 1N hydrochloric acid. The pH is adjusted to 3.2 with 1N hydrochloric acid and the solid N-[6-(4-pyridyl)-1,2-dihydro-2-oxonicotinyl]amoxicillin is collected by filtration and washed well with ice water. This amoxicillin derivative is suspended in 250 ml. of cold water and the pH is adjusted to 6.3 with 1N aqueous sodium hydroxide. The resulting solution is clarified by filtration and the filtrate is lyophilized to give the sodium salt of N-[6-(4-pyridyl)-1,2-dihydro-2-oxonicotinyl]amoxicillin; $[\alpha]_D^{23} = +212°$ (1.02% in 75% dimethylformamide-pyridine).

Starting Materials (a) Amoxicillin Dimethyl Sulfoxide Complex

A 90 g. portion of amoxicillin trihydrate is pulverized under a layer of methylene chloride, filtered, washed with methylene chloride and ether, then suspended in 650 ml. of dimethyl sulfoxide. The mixture is stirred at room temperature for 2.5 hours, 100 ml. of methylene chloride is added and the mixture cooled to 0°–5° C. The solid product is collected by filtration, washed with methylene chloride and ether, and dried for 16 hours at room temperature under high vacuum. Analysis shows 3.6 moles of dimethyl sulfoxide by n.m.r. and 1 mole of water by Karl Fisher titration, for each mole of amoxicillin.

(b) 6-(4-Pyridyl)-1,2-dihydro-2-oxonicotinylimidazolide

To a stirred suspension of 10.8 g. of 6-(4-pyridyl)-1,2-dihydro-2-oxonicotinic acid (U.S. Pat. No. 3,873,523) in 120 ml. of N,N'-dimethylacetamide is added 11.5 g. of 1,1'-carbonyldiimidazole. The mixture is stirred and heated to 60° C., then allowed to cool as stirring is continued over a 3 hour period. The resulting precipitate of 6-(4-pyridyl)-1,2-dihydro-2-oxonicotinylimidazolide is collected by filtration, washed with ether and dried; m.p. 228°–229° C. dec.

EXAMPLE 2

A stirred suspension of 1.1 g. of D-(+)-N-[6-(4-pyridyl)-1,2-dihydro-2-oxonicotinyl]-2-(p-hydroxyphenyl)glycine in 25 ml. of methylene chloride is cooled to 0° C. and 5 ml. of dimethylformamide is added, followed by 1.1 ml. of N-methylmorpholine. After stirring at 0° C. for 15 minutes, the mixture is cooled to −40° C. and a solution of 0.52 ml. of isobutyl chloroformate in 4.5 ml. of methylene chloride is added. The mixture is stirred for 6 minutes then added to a solution of 1.9 g. of the trimethylsilyl ester of 6-aminopenicillanic acid in 6 ml. of methylene chloride. The mixture is stirred at −40° C. for 30 minutes, then allowed to warm to −15° C. while stirring an additional hour. The mixture is added to 150 ml. of chipped ice and water and the pH adjusted to 3.0 with 1N hydrochloric acid. The solid N-[6-(4-pyridyl)-1,2-dihydro-2-oxonicotinyl]amoxicillin is collected by filtration and washed with water. This amoxicillin derivative is suspended in 20 ml. of cold water and the pH is adjusted to 6.5 with 1N aqueous sodium hydroxide. The resulting solution is clarified by filtration and the filtrate is lyophilized to give the sodium salt of N-[6-(4-pyridyl)-1,2-dihydro-2-oxonicotinyl]amoxicillin.

Starting Materials (a) 6-(4-Pyridyl)-1,2-dihydro-2-oxonicotinyl Chloride Hydrochloride A mixture of 13 g. of 6-(4-pyridyl)-1,2-dihydro-2-oxonicotinic acid (U.S. Pat. No. 3,873,523) and 90 ml. of thionyl chloride is stirred at room temperature for 16 hours, then diluted with 250 ml. of hexane. The resulting precipitate of 6-(4-pyridyl)-1,2-dihydro-2-oxonicotinyl chloride hydrochloride is collected by filtration, washed with hexane and dried.

(b) D-(+)-N-[6-(4-Pyridyl)-1,2-dihydro-2-oxonicotinyl]-2-(p-hydroxyphenyl)glycine A stirred suspension of 1.67 g. of D-(−)-2-(p-hydroxyphenyl)glycine in 30 ml. of N,N-dimethylacetamide is cooled to 3° C. and 3.8 ml. of dichlorodimethylsilane is added, followed by 4.2 ml. of triethylamine. The mixture is stirred at room temperature for 45 minutes, cooled to 0°–5° C. and treated with 2.7 g. of 6-(4-pyridyl)-1,2-dihydro-2-oxonicotinyl chloride hydrochloride, followed by 2.8 ml. of triethylamine. The mixture is stirred at 0°–5° C. for 30 minutes, allowed to stand at 10° C. for 48 hours, then stirred at room temperature for 4 hours. The mixture is poured into 300 ml. of ice water and the pH is adjusted to about 2.5. The resulting precipitate of D-(+)-N-[6-(4-pyridyl)-1,2-dihydro-2-oxonicotinyl]-2-(p-hydroxyphenyl)glycine is collected by filtration, washed with water and dried; m.p. 183° dec., after crystallization from aqueous methanol.

To a stirred suspension of 16.7 g. D-(−)-2-(p-hydroxyphenyl)glycine and 1100 ml. of methylene chloride is added 38.4 ml. of chlorotrimethylsilane followed by 42 ml. of triethylamine over a 20 minute period. The mixture is stirred for 1 hour at room temperature and then the solution is cooled to 0°–5° C. and 26.4 g. of 6-(4-pyridyl)-1,2-dihydro-2-oxonicotinyl chloride hydrochloride is added in portions. A solution of 25.2 ml. of triethylamine and 100 ml. of methylene chloride is added over a 1 hour period at 0°–5° C. Stirring is continued for 3 hours at 0°–5° C., and then at room temperature overnight. The methylene chloride is evaporated under reduced pressure and the residue is dissolved in a solution of 500 ml. water and 100 ml. 2N hydrochloric acid. The solution is clarified by filtration and the pH of the filtrate is adjusted to 3.0 with 2N aqueous sodium hydroxide. The resulting precipitate of D-(+)-N-[6-(4-pyridyl)-1,2-dihydro-2-oxonicotinyl]-2-(p-hydroxyphenyl)-glycine is collected by filtration, washed with water, and dried; m.p. 195–205 dec., $[\alpha]_D^{23} = +50$ (1% in 1N hydrochloric acid), after crystallization from aqueous acetonitrile.

I claim:
1. A compound of the formula

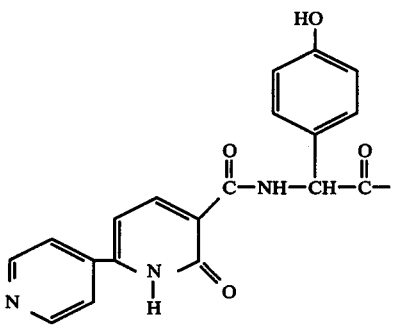

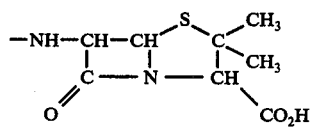

and pharmaceutically-acceptable salts thereof.

2. The compound of claim 1 which is N-[6-(4-pyridyl)-1,2-dihydro-2-oxonicotinyl]amoxicillin.

3. The compound of claim 1 which is the sodium salt of N-[6-(4-pyridyl)-1,2-dihydro-2-oxonicotinyl]amoxicillin.

* * * * *